United States Patent
Terrio

(10) Patent No.: US 9,168,165 B2
(45) Date of Patent: Oct. 27, 2015

(54) SQUAT AND LUNGE TRAINING DEVICE

(76) Inventor: Timothy Terrio, Bakersfield, CA (US)

(*) Notice: Subject to any disclaimer, the term of this patent is extended or adjusted under 35 U.S.C. 154(b) by 1228 days.

(21) Appl. No.: 12/765,841

(22) Filed: Apr. 22, 2010

(65) Prior Publication Data
US 2010/0274166 A1  Oct. 28, 2010

Related U.S. Application Data

(60) Provisional application No. 61/214,388, filed on Apr. 22, 2009.

(51) Int. Cl.
| | |
|---|---|
| *A61F 5/00* | (2006.01) |
| *A61F 13/00* | (2006.01) |
| *A61F 5/01* | (2006.01) |
| *A63B 23/04* | (2006.01) |
| *A63B 69/00* | (2006.01) |
| *A63B 71/00* | (2006.01) |

(52) U.S. Cl.
CPC ........... *A61F 5/0113* (2013.01); *A63B 23/0405* (2013.01); *A63B 69/0059* (2013.01); *A63B 71/0054* (2013.01); *A63B 2023/0411* (2013.01); *A63B 2069/0062* (2013.01); *A63B 2071/0072* (2013.01)

(58) Field of Classification Search
CPC ... A61F 5/0113; A61F 5/0111; A61F 5/0193; A63B 71/0054; A63B 69/0059; A63B 34/0405; A63B 2023/0411; A63B 71/0072; A63B 2069/0062
USPC .......... 128/869, 882; 602/5, 6, 12, 23, 24, 25, 602/62, 65, 160, 27–29, 10, 32; 482/79, 482/120–124, 907, 148, 82; 2/22; D24/169, D24/190–192
See application file for complete search history.

(56) References Cited

U.S. PATENT DOCUMENTS

| | | | | |
|---|---|---|---|---|
| 2,717,387 | A * | 9/1955 | McMahan | 2/22 |
| 3,504,668 | A * | 4/1970 | Boudon | 602/28 |
| 4,320,748 | A * | 3/1982 | Racette et al. | 602/23 |
| 4,497,070 | A * | 2/1985 | Cho | 2/22 |
| 5,219,324 | A * | 6/1993 | Hall | 602/28 |
| 6,019,741 | A * | 2/2000 | Prieskorn | 602/5 |
| 7,090,629 | B1 * | 8/2006 | Abbou | 482/148 |
| 2009/0227928 | A1 * | 9/2009 | Drake et al. | 602/28 |

* cited by examiner

Primary Examiner — Kim M Lewis
(74) Attorney, Agent, or Firm — R. Scott Kimsey, Esq.; Klein DeNatale Goldner

(57) ABSTRACT

A device which restricts movement of the knee during lunge and squatting exercises prevents weight imbalance which may result in undue strain and knee injury. The device has a foot engagement member stepped upon by the user and held in place by the user's weight, or the foot engagement member conforms to the side of the user's foot and is held in place by a strap. Attached to the foot engagement is a vertical member extending upwardly from the foot engagement member. A shin engagement member attached to the vertical member is generally positioned in a position along the lower leg of the user, below the knee and laterally adjacent to the user's tibia. As the user performs exercise, the shin engagement member prevents the user's knees from forward movement which extends forward of the user's feet. The device also has structure which prevents inward collapse of the knees.

2 Claims, 5 Drawing Sheets

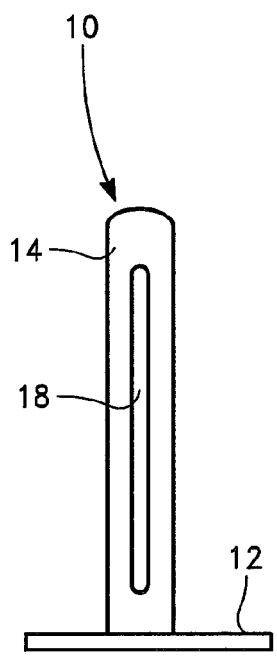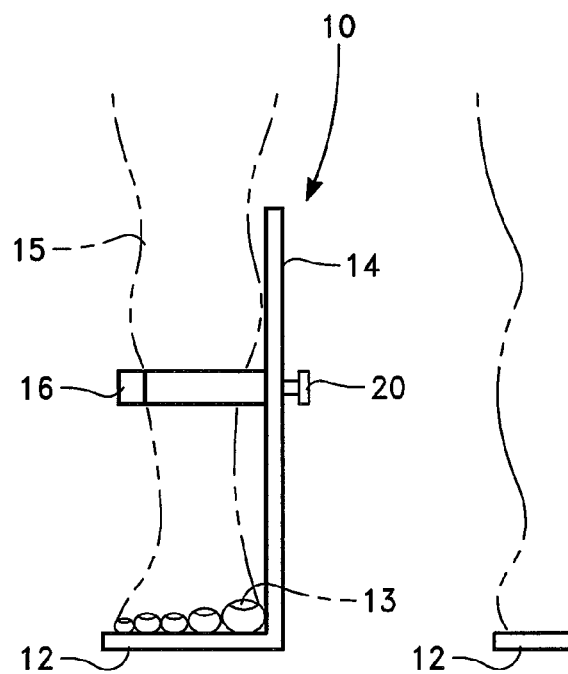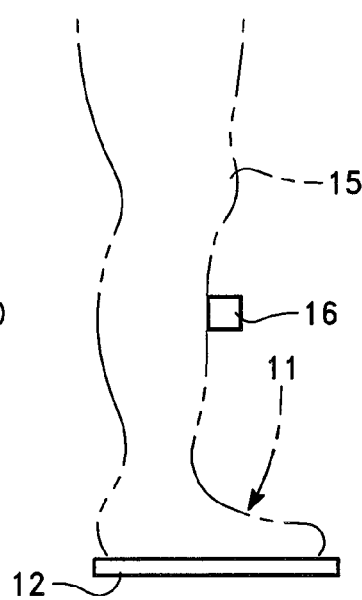
FIG. 1    FIG. 2    FIG. 3
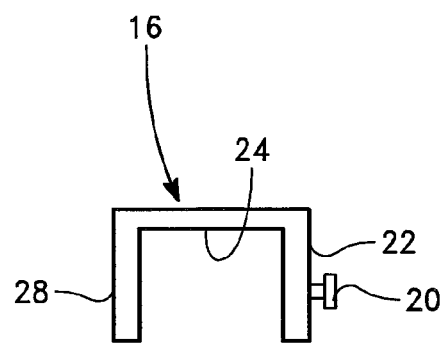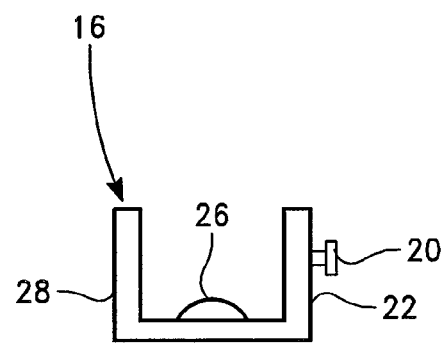
FIG. 4    FIG. 5

SQUAT AND LUNGE TRAINING DEVICE

CROSS-REFERENCE TO RELATED APPLICATION

U.S. Provisional Application No. 61/214,388 for this invention was filed on Apr. 22, 2009, for which application this inventor claims domestic priority.

BACKGROUND

The disclosed device generally relates to devices used during physical exercise and rehabilitation and specifically to devices to strengthen the lower body and leg muscles by assisting in the safe and proper execution of squat and lunge exercises.

Various exercises are utilized for toning, strengthening, and rehabilitating muscles of the lower body. Among these exercises are squats and lunges. In a properly performed squat, a repletion of the exercise has the person starting in a standing position with his or her feet flat on the floor, mat, etc. with their feet spread approximately a shoulder width apart with his or her toes pointing forward. The person thereafter pushes his or her hips rearward and begins to bend at the knees, while simultaneously maintaining the lower legs a substantially motionless position. The person continues to bend at the knees until the top of his or her have descended below the top of their knees. The repetition is completed by rising back to a standing position A similar exercise is the lunge, which focuses on each individual leg. In the lunge, the person starts in a standing position with his or her feet flat on the ground surface, with the toes of each foot generally pointing forward, with one leg in front of the other. The person thereafter pushes leans forward on the front leg, simultaneously bending the knee of the front leg, and shifting the rear foot from being flat on the floor, to where the heel of the rear foot is raised. The person continues to lean forward and bending the front knee until the thigh of the front leg is substantially parallel to the ground surface. The repetition is completed by rising back to a standing position. In the proper performance of the lunge, the person's front knee does not extend forward of the toes of the front foot and the knee does not turn inward.

When performed properly squats, lunges and similar leg exercises result in toning of lower body and leg muscles such as the glutes, the hamstrings and the quads. However, if not properly performed however, squats, lunges, and similar exercises can lead to pain and even injury. For example, during the execution of a squat exercise, it is very important to assure that the knees are not thrust forward beyond the toes of the feet, and that the legs do not collapse inwardly. The result of moving the knees beyond the toes or allowing the knees to collapse inwardly can be undue strain and even injury to the knees.

SUMMARY OF THE INVENTION

Embodiments of the presently disclosed invention assist in the safe and proper execution of squat and lunge exercises in that the invention effectively precludes movement of the knees forward beyond the toes, thereby preventing the weight imbalance and resulting undue strain and knee injury. Embodiments of the invention also prevent the inward collapse of the knees during these exercises. The maintenance of the knees in the appropriate position relative to the toes during the execution of squats and lunges improves safety and ease of execution. Embodiments of the disclosed device provides a relatively simple item of exercise equipment that is easily employed in the performance of a safe and proper squat and lunge exercises. Additionally, embodiments of the device provides compact, portable, easily used items of exercise equipment for accomplishing and achieving the proper execution of squat and lunge exercises.

Depending upon the exercise, one or two of the devices are utilized. A generic form of the device for performing squats comprises a pair of foot engagement members, where each foot engagement member engages one of the users feet, while at least a portion of the foot engagement member simultaneously engages the ground surface upon which the person is exercising. The device further comprises a pair of vertical members, where each vertical member is attached to a corresponding foot engagement member. The structure of the vertical members is such that each of the vertical members remain substantially stationary during the repetition of the squatting exercise. A pair of shin engagement members are each attached to a corresponding vertical member. During the squatting exercise, each of the shin engagement members abuts a portion of the lower front of each of the person's legs. The shin engagement members have a structure which restricts forward movement of the person's knees as the person progresses through the exercise.

The apparatus further comprises means for restricting inward movement of the user's knees towards one another during the repetition of the squatting exercise. In the first embodiment, the means for preventing inward movement is a side member which is part of each shin engagement member. In the second embodiment, the foot engagement member comprises an outwardly extending support member. The foot engagement member of the second embodiment engages the inside portion of each of the user's feet, such that the outwardly extending support member prevents the user's feet from rotating inwardly, which occurs when the knees collapse toward one another.

The apparatus further comprises means for retaining the device in engagement with the legs of the user. In the first embodiment, the apparatus is retained in engagement with the legs of the user by the user standing upon a portion of the foot engagement member, such that the weight of the user holds the device in position. In the second embodiment, the means for retaining the device in engagement with the legs of the user comprises straps which, when a pair of devices is utilized for performing squats, secure an apparatus to each of the user's legs.

In the first embodiment, the shin engagement member may be releasably positionable to allow placement of the shin engagement member at the correct position along the vertical member for the person using the device.

BRIEF DESCRIPTION OF THE DRAWINGS

FIG. 1 shows a side view of the first embodiment of the present training device.

FIG. 2 shows a front view of the first embodiment of the present device, showing the positioning of the leg of a user.

FIG. 3 shows another side view of the first embodiment of the present training device, showing the positioning of the leg of a user.

FIG. 4 shows a top view of an embodiment of the shin engagement member of the first embodiment of the present training device.

FIG. 5 shows a bottom view of the shin engagement member of FIG. 4.

DETAILED DESCRIPTION OF THE EMBODIMENTS

Figure 6:
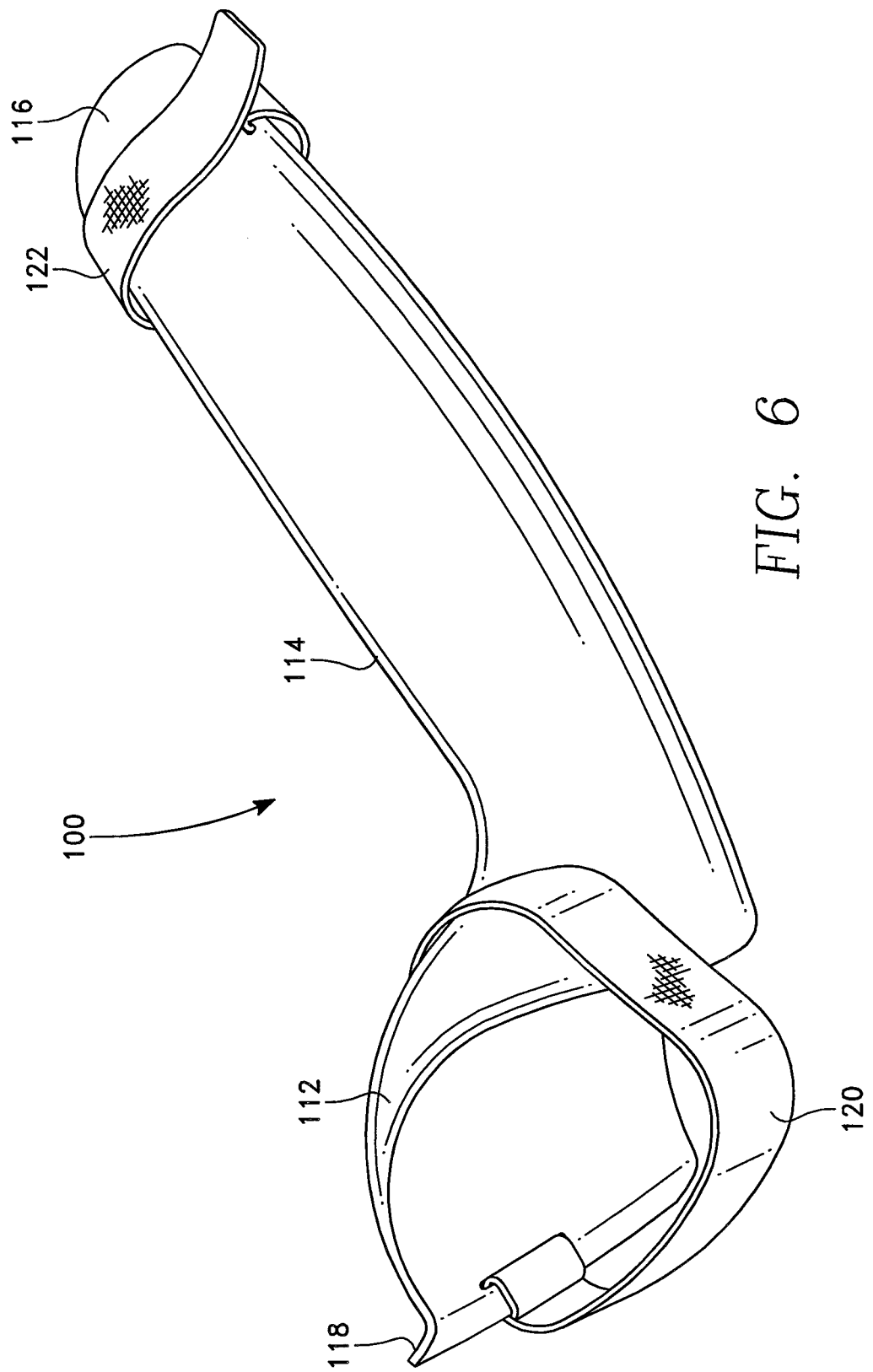
FIG. 6 shows a perspective view of the second embodiment of the present training device, showing the exterior side of the integral device.
Figure 7:
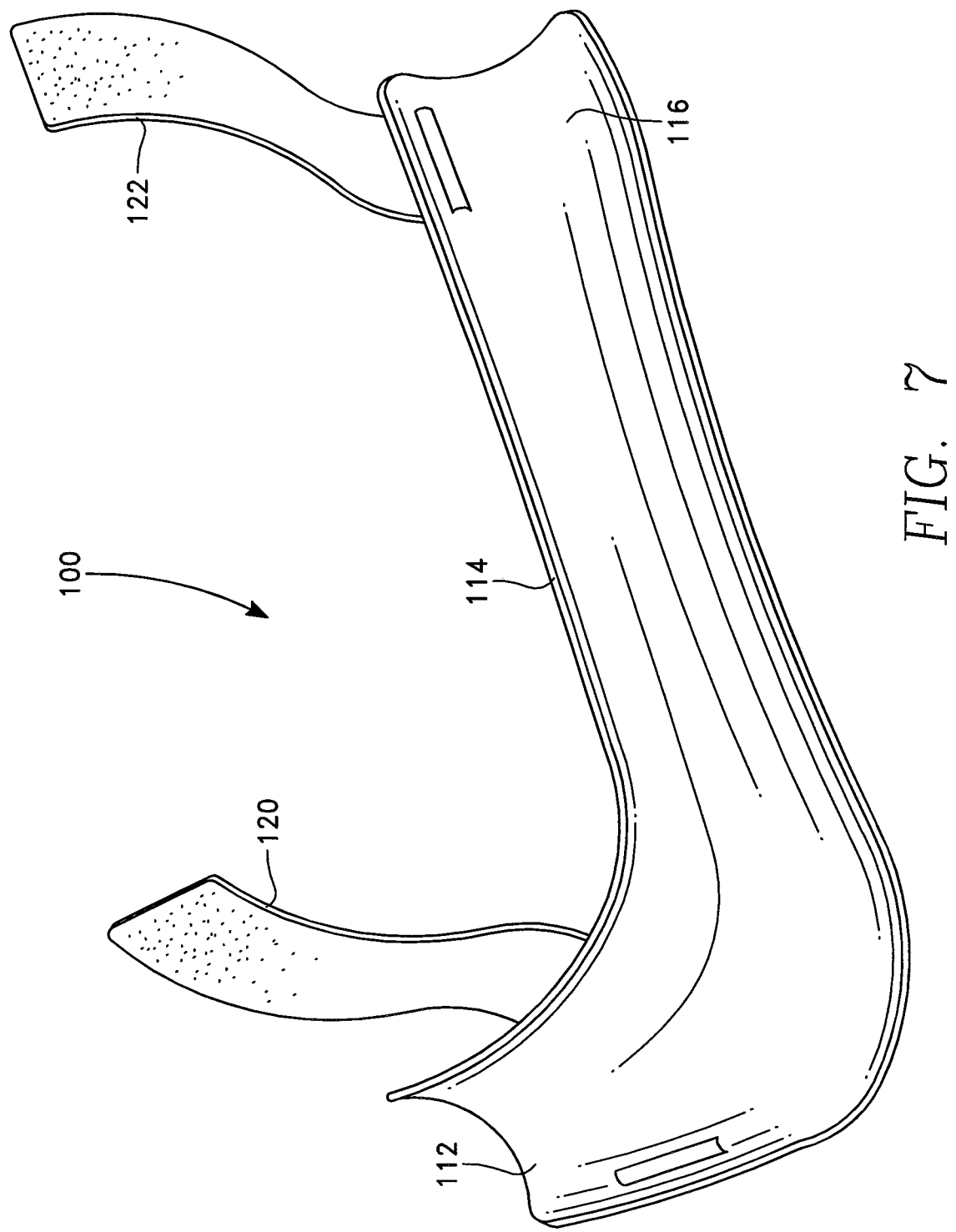
FIG. 7 shows a perspective view of the second embodiment of the present training device, showing the interior side of the integral device.
Figure 8:
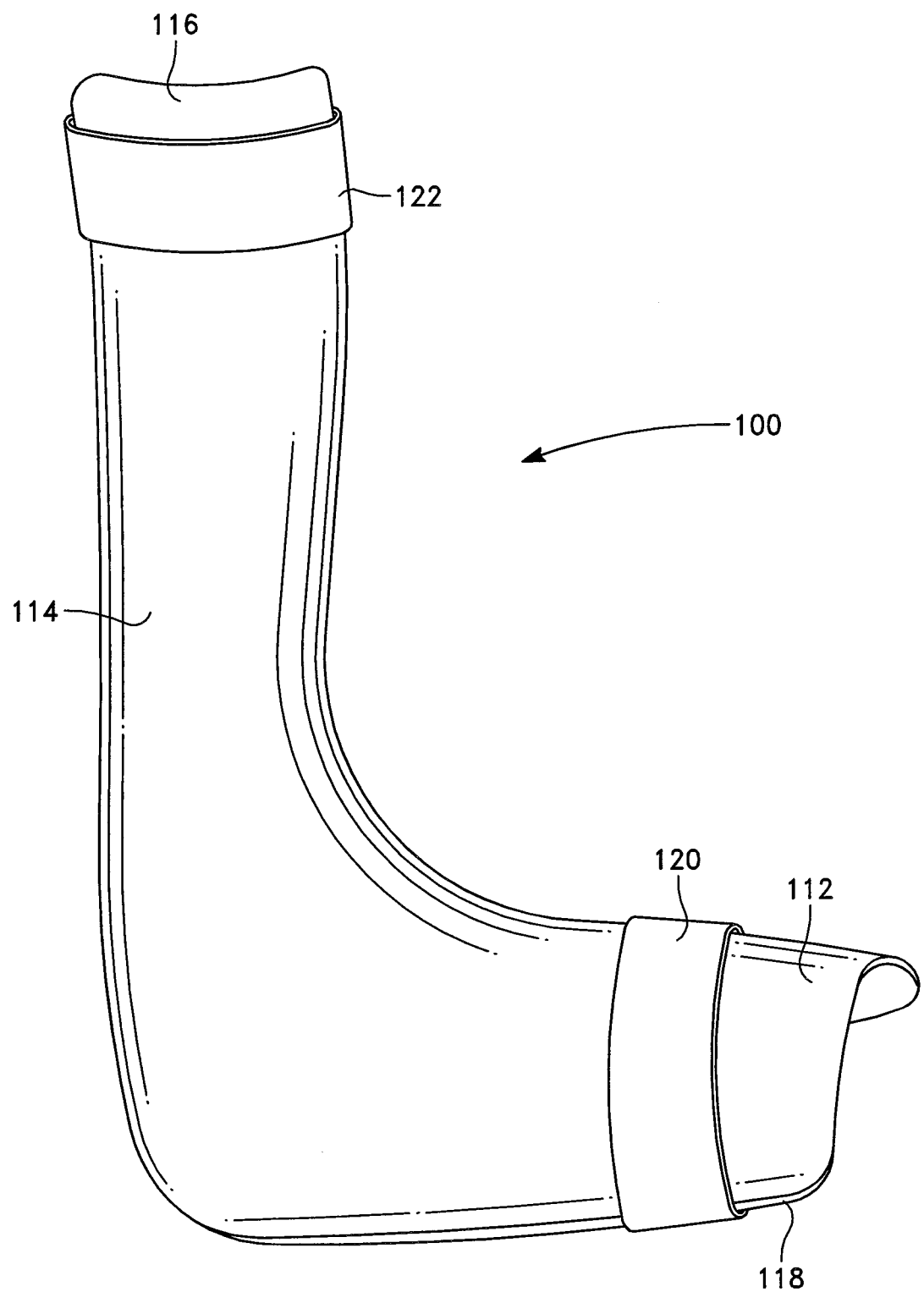
FIG. 8 shows an elevational view of the second embodiment of the present training device, showing the exterior side of the integral device.

Referring now to the Figures, FIGS. 1 through 5 show various views of the first embodiment 10 of the disclosed training device. The first embodiment 10 training device 10 comprises a generally horizontal foot engagement member 12, a vertical member 14 which extends upwardly from the foot engagement member, and a shin engagement member 16 attached to the vertical member 14. Shin engagement member 16 is generally positioned in a position along the lower leg of the user, below the knee and laterally adjacent to the user's tibia.

In performing a squat with the first embodiment 10, the user stands with their foot 11 placed atop the foot engagement member 12, with the toes 13 of the foot 11 facing forward, as opposed to rotated either inwardly or outwardly. In performing a single repetition of a squat with this embodiment, the user starts in a standing position with his or her feet flat and spread approximately a shoulder width apart with his or her toes pointing forward as shown in FIG. 2. The user thereafter pushes his or her hips rearward and begins to bend at the knees, maintaining the lower legs substantially motionless. The user continues to bend at the knees until the top of the user's hips have descended below the top of the user's knees. In this position, the user's thighs are generally parallel with the floor. The repetition is completed by rising back to a standing position. In the proper performance of the above described repetition, the user's knees do not extend forward of the user's toes and do not turn inward. Embodiments of the disclosed apparatus are configured to enable a user to easily achieve this correct performance.

In performing a lunge, the user starts in a standing position with his or her feet flat on the ground surface, with the toes of each foot generally pointing forward, with one leg in front of the other. The person thereafter pushes leans forward on the front leg, simultaneously bending the knee of the front leg, and shifting the rear foot from being flat on the floor, to where the heel of the rear foot is raised. The person continues to lean forward and bending the front knee until the thigh of the front leg is substantially parallel to the ground surface. The repetition is completed by rising back to a standing position. In the proper performance of the lunge, the person's front knee does not extend forward of the toes of the front foot and the knee does not turn inward. It is to be appreciated that when used for both the squat and lunge, and other exercises where it is important to restrict the movement of the knees with respect to the position of the feet, embodiments of the present invention may be utilized.

The vertical member 14 of the first embodiment 10 may comprise an elongate slot 18 which extends through the vertical member 14 and traverses a section of the vertical length of the vertical member 14 as shown in FIG. 1. The shin engagement member 16 may further comprise releasable engagement means 20 which allow the shin engagement member of the first embodiment to be repositioned along elongate slot 18 as desired and suitable for the user. The shin engagement member 16 of the first embodiment further comprises a front member 24 which limits forward movement of the user's knees and a side member 22 which restricts inward movement of the user's knees 15 during the repetition of the squatting exercise. The restriction of the inward movement of the user's knees prevents the person's knees from collapsing inwardly during a squat or lunge exercise, which is not an uncommon occurrence without the use of a support device. The shin engagement member 16 may also comprise a side member 28 which restricts outward movement of the user's knees during the repetition of the squatting exercise.

The releasable engagement means 20 may extend through side member 22 and through elongate slot 18, thereby allowing shin engagement member 16 to be positioned as needed to allow the device to fit different users of the equipment. The releasable engagement means 20 engages the slot 18, and allows the shin engagement member 16 to be adjustably positioned along the height of the vertical member 14. The engagement means 20 allows for positioning of the shin engagement member 16 at any height along the slot 18. The engagement means 20 may comprise a nut and bolt arrangement or any of the commonly known and used retention means. The shin engagement member 16 may further comprise a cushion or padding member 26 which faces the knee or shin. The cushion 26 serves to assist in preventing rubbing by the shin or knee against the shin engagement member 16. The components of the first embodiment 10 will generally be fashioned from materials having sufficient rigidity and strength to perform the required function, such as steel, stainless steel, aluminum, carbon fiber, etc.

A second embodiment 100 of the disclosed training device is shown in FIGS. 6 through 9. While visually distinct from the first embodiment 10, it is to be appreciated that the second embodiment comprises functionally equivalent elements of the first embodiment. The second embodiment comprises a foot engagement member 112, a vertical member 114 which extends upwardly from the foot engagement member, and a shin engagement member 116 attached to the vertical member 114. Shin engagement member 116 is generally positioned in a position along the lower leg of the user, below the knee 115, and laterally adjacent to the user's tibia. As can be seen in FIGS. 6 through 9, in the second embodiment 100, the foot engagement member 112, the vertical member 116, and the shin engagement member are an integral unit.

Figure 9:
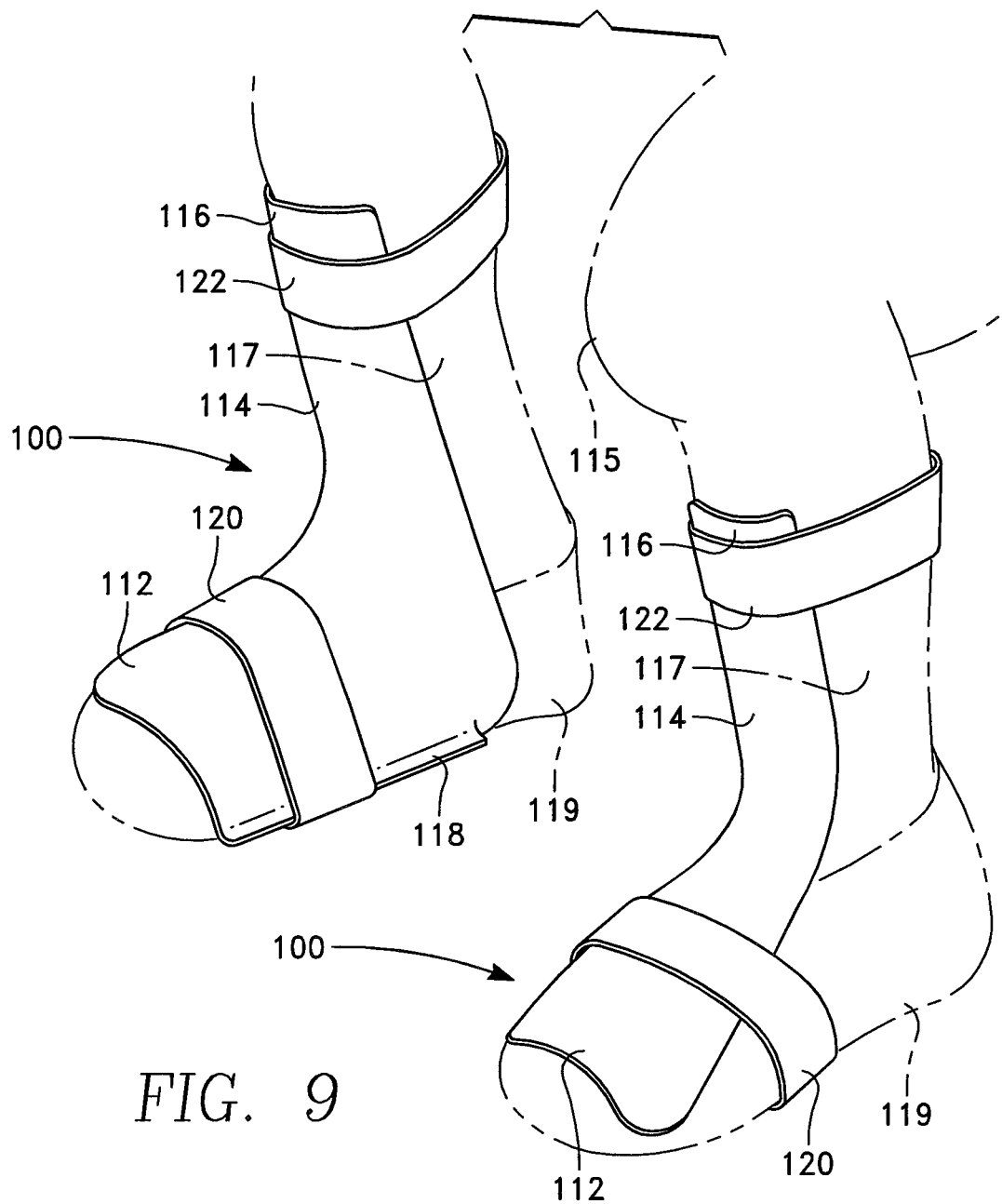
FIG. 9 shows a user performing a squat with the second embodiment of the present training device on each leg.

The vertical member 114 of the second embodiment 100 comprises a structure which causes the vertical member to remain substantially stationary during the repetition of a leg exercise, such as a squat or lunge. In the second embodiment 100, the vertical member 114 is of a molded construction to conformably engage a portion of the lower front of the user's leg 117, as shown in FIG. 9. As further shown in FIG. 9, this structure restricts forward movement of the user's knee (or knees, depending upon the exercise), where the vertical member 114 abuts the user's leg below the knee 115.

The foot engagement member 112 of embodiment 100 comprises a rigid structure molded to conformably engage to an inside edge of the user's feet 119. In this embodiment, the inward movement of the knees 115 is restricted during the exercise by a support member 118 which laterally extends on the inside of the foot engagement member 112. It is to be appreciated that the position of support member 118 will be different on an embodiment 100 used on the left leg as opposed to the that used on the right leg. Thus, embodiment 100 requires a left side device and a right side device.

Embodiment 100 comprises straps 120, 122 as a means for retaining the device in engagement with the user's legs. A first strap 120 engages the foot engagement member 112 to the user's foot 119 and a second strap 122 attaches the shin engagement member 112 to the lower leg of the user, below the knee and about the calve. Hook and loop fasteners may be utilized with the straps to provide an expeditious mechanism for attaching and removing the device.

Because of its molded configuration, embodiment 100 will generally be fabricated from materials which are easily moldable, such as plastic. It might also be fabricated from fiberglass and carbon fiber materials. The inside surfaces may be cushioned to make the device more comfortable for the user.

While a single device of either embodiment 10 or embodiment 100 could be utilized to ensure correct form for a lunge, a pair of the devices will typically be utilized for squats.

While the above is a description of various embodiments of the present invention, further modifications may be employed without departing from the spirit and scope of the present invention. Thus the scope of the invention should not be limited by the specific structures disclosed. Instead the true scope of the invention should be determined by the following appended claims.

What is claimed is:

1. A device for assisting a human user in properly performing a leg exercise, the leg exercise of the type where, for a single repetition of the exercise, the user starts in a standing position with his or her feet flat on a ground surface, with the toes of each foot pointing forward, the user thereafter leans forward on a first leg attached to a first foot, and begins to bend at a first knee of the first leg and continuing to bend at the first knee until a portion of the first leg about the first knee is substantially parallel to the ground surface, and completing the repetition by rising back to a standing position, wherein, in the proper performance of the above described repetition, the user's first knee does not extend forward of the toes of the first foot and does not turn inward, the device comprising:
    a rigid foot engagement member sized and shaped to engage the first foot the foot engagement member defining an open bottom such that the first foot of the user contacts the ground surface when said device is in use and wherein the foot engagement member is adapted to contact only a top and an inside edge of the user's foot;
    a rigid shin engagement member attached to the vertical member, the shin engagement member sized and shaped to abut a portion of the lower front of the first leg, the shin engagement member comprising structure which restricts forward movement;
    a rigid round surface support member extending laterally from the foot engagement member and oriented such that the ground surface support member extends parallel to the ground when a wearer of the device is standing on the ground, thereby restricting inward movement of the user's knee; and
    means for retaining the device in engagement with the first leg.

2. A system for assisting a human user in properly performing a squatting exercise, the squatting exercise of the type where, for a single repetition of the exercise, the user starts in a standing position with his or her feet flat and spread approximately a shoulder width apart with his or her toes pointing forward, the user thereafter pushes his or her hips rearward and begins to bend at the knees, maintaining the lower legs substantially motionless, continuing to bend at the knees until the top of the user's hips have descended below the top of the user's knees, and completing the repetition by rising back to a standing position, wherein, in the proper performance of the above described repetition, the user's knees do not extend forward of the user's toes and do not turn inward, the system comprising:
    a pair of rigid foot engagement members each sized and shaped to engage one of the user's feet, the foot engagement members each defining an open bottom such that the feet of the user contacts a ground surface when said device is in use and wherein each foot engagement member is adapted to contact only a top and an inside edge of the user's foot;
    a pair of rigid vertical members, each attached to a corresponding foot engagement member, the vertical members each comprising structure which causes each vertical member to remain substantially stationary during the repetition of the squatting exercise;
    a pair of rigid shin engagement members each attached to a corresponding vertical member, each shin engagement member sized and shaped to abut a portion of the lower front of one of the user's legs, the shin engagement members comprising structure which restricts forward movement of the user's knees during the repetition of the squatting exercise,
    a pair of rigid ground surface support members extending, each extending laterally from a respective foot engagement member, the pair of ground support members oriented to extend parallel to the ground when a user of the system is standing on the ground, thereby restricting inward movement of the user's knee; and
    means for retaining the foot engagement members in engagement with the feet of the user.

* * * * *